United States Patent [19]
Asahina et al.

[11] Patent Number: 5,073,914
[45] Date of Patent: Dec. 17, 1991

[54] STEREOSCOPIC X-RAY APPARATUS

[75] Inventors: Hiroshi Asahina, Tochighi; Hiroshi Yasuhara, Ootawara, both of Japan

[73] Assignee: Kabushiki Kaisha Toshiba, Kawasaki, Japan

[21] Appl. No.: 604,460

[22] Filed: Oct. 29, 1990

[30] Foreign Application Priority Data

Oct. 30, 1989 [JP] Japan ................................ 1-282313

[51] Int. Cl.$^5$ .......................................... G21K 4/00
[52] U.S. Cl. ...................................... 378/42; 378/99
[58] Field of Search ........................... 378/41, 42, 99; 358/111

[56] References Cited
U.S. PATENT DOCUMENTS 4,819,255 4/1989 Sato ........................................ 378/42

Primary Examiner—Craig E. Church
Attorney, Agent, or Firm—Finnegan, Henderson, Farabow, Garrett, and Dunner

[57] ABSTRACT

A stereoscopic X-ray apparatus is provided in which X-rays are irradiated from the two foci of a stereoscopic X-ray tube to an object to be examined so as to obtain images of the object picked-up in two directions and which permits the object to be stereoscopically displayed based on the two picked-up images. X-ray images having passed the object are picked-up by an image intensifier tube and a TV camera and stored into two frame memories. The two images output from the frame memories are alternately displayed on a display unit. At this time, the positional relation between the object and the X-ray tube and the positional relation between the object and the image intensifier tube set at the picking-up time are compared with those set in the standard state, the display positions of the two images are shifted in the right and left directions by the same distance equal to half the difference therebetween so as to adjust parallax of the two images which corresponds to the stereoscopy, thus making it possible to stereoscopically display the two images with the desired stereoscopy.

11 Claims, 7 Drawing Sheets

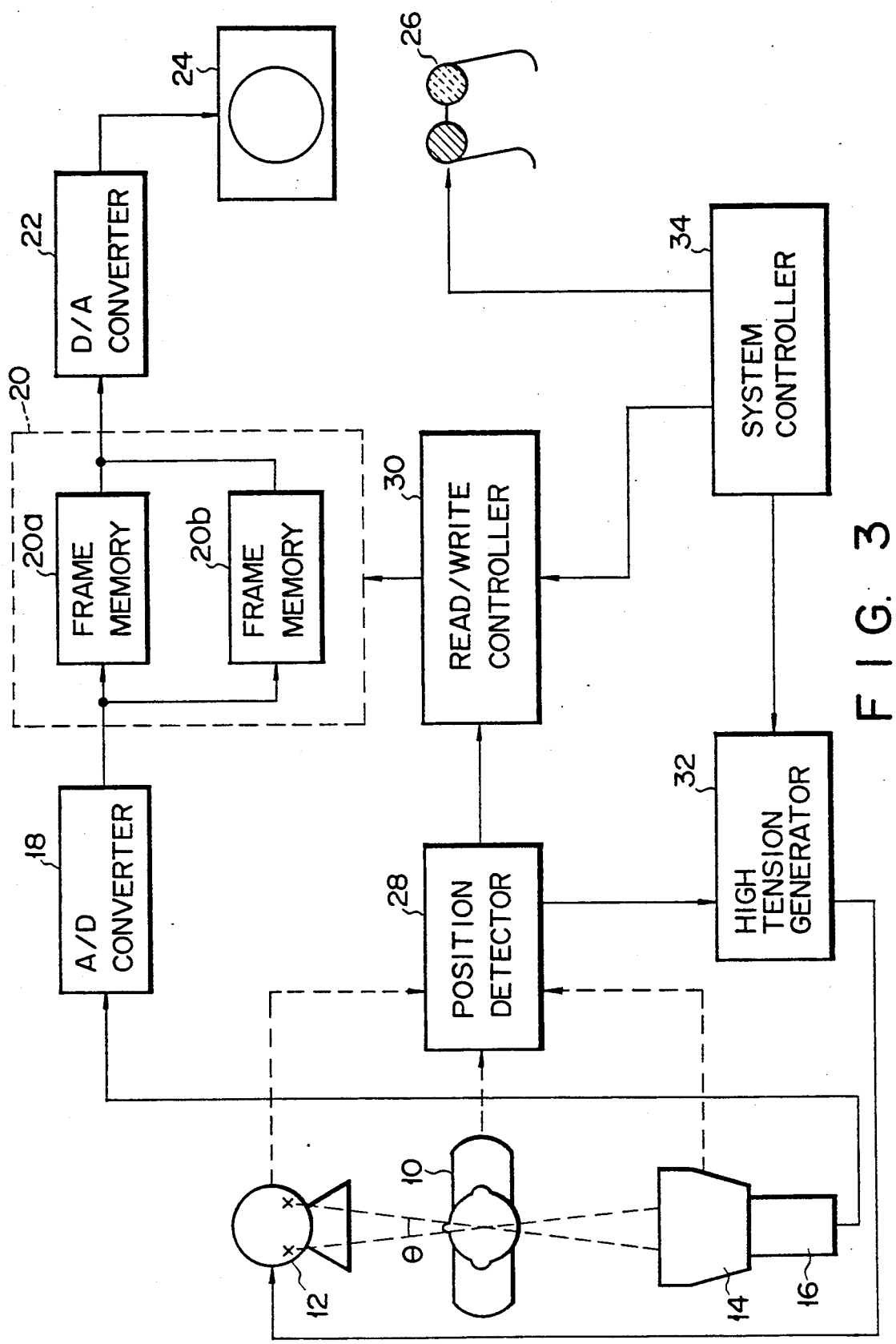
F I G. 3

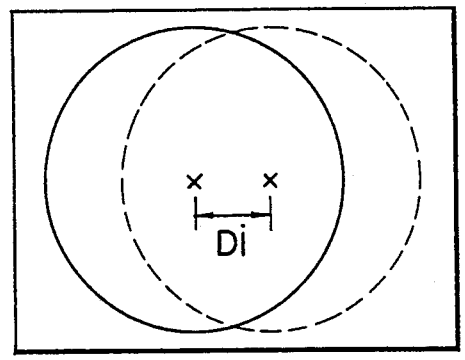
F I G. 4A
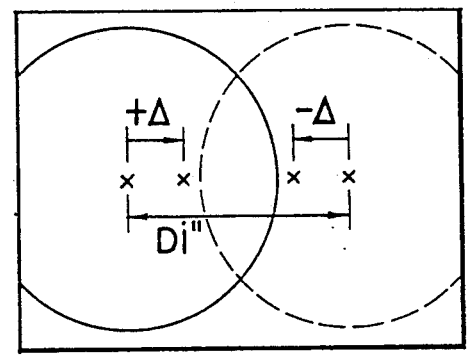
F I G. 4B
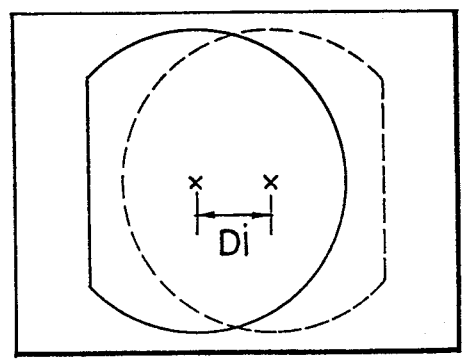
F I G. 4C

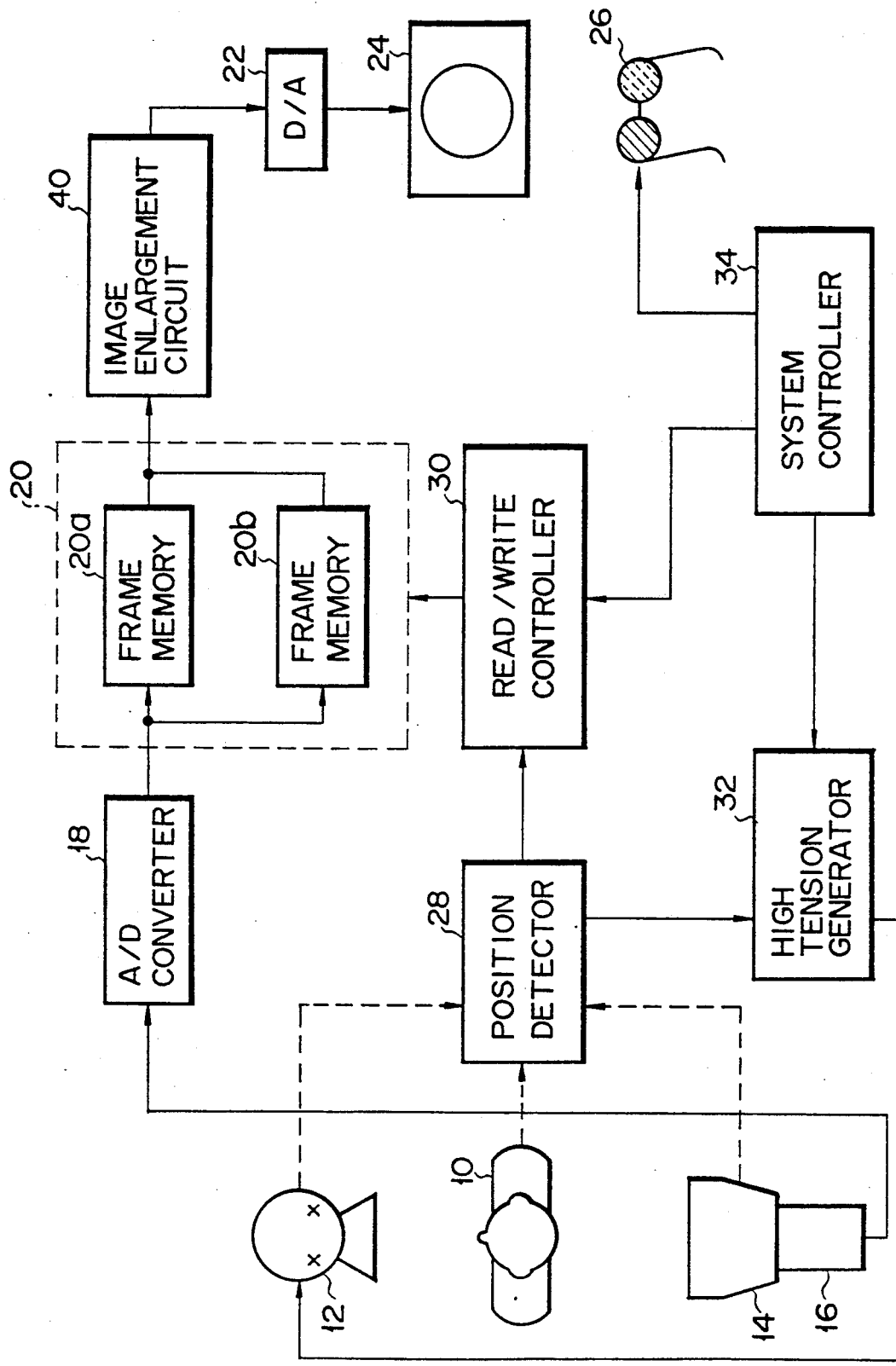
F I G. 5

STEREOSCOPIC X-RAY APPARATUS

BACKGROUND OF THE INVENTION

1. Field of the Invention

This invention relates to a stereoscopic X-ray apparatus for irradiating X-rays from right and left portions in two directions to intersect at a to-be-examined object by using a stereoscopic X-ray tube or the like and using X-ray images obtained in the above two directions so as to permit the object to be stereoscopically observed.

2. Description of the Related Art

As an example of a conventional stereoscopic X-ray apparatus, an X-ray apparatus is known in which X-rays are sequentially irradiated from two foci of a stereoscopic X-ray tube and two X-ray images obtained by two X-ray irradiations are photographed on two X-ray films. The X-ray films after being subjected to development are placed side by side on a film viewer and the object may be stereoscopically observed by using the parallax between the two images.

In recent years, digital fluorography is widely used, and in this case, an X-ray image having passed an object to be examined is picked up by means of an image intensifier tube and TV camera and picked-up images created by X-rays from the right and left foci are stored into an image memory. Then, the picked-up images created by X-rays from the right and left foci and read out from the image memory are displayed on two display units. Also, in this case, the object can be stereoscopically observed in the same manner as in the case of using the films. The stereoscopic display method in the digital fluorography includes a dynamic stereoscopic display method which requires use of field switcher glasses with electronic shutters and in which right and left images are alternately displayed on a single display unit and the electronic shutters are alternately driven in synchronism with alternate display of the images in addition to a static stereoscopic display method in which two images are simultaneously displayed on the two display units as described above.

In the above conventional cases, since the stereoscopy is determined by the parallax between the images, it can be determined by a distance between the foci of the stereoscopic X-ray tube, which is generally a fixed value, a distance between the image intensifier tube (or film) and the X-ray tube, and a distance between the image intensifier tube (or film) and the object. The latter two distances change according to the image pick-up condition (geometrical relation among the X-ray tube, object, and image intensifier tube). Therefore, the stereoscopy is determined by the image pick-up condition and it will be changed according to the image pick-up condition. Further, since the sensitivity to the stereoscopy may be different for different persons, it sometimes happens that the stereoscopy of the same stereoscopic display image is sufficiently high for one person but may be low for another. In this case, if the stereoscopy is low, the positional relation in the depth direction between two things may be erroneously recognized.

SUMMARY OF THE INVENTION

An object of the present invention is to provide a stereoscopic X-ray apparatus capable of adjusting the stereoscopy at the time of stereoscopic observation after imaging an object to be examined irrespective of the imaging condition (positional relation among an X-ray tube, object, and image intensifier tube) so as to provide a desired stereoscopy under any imaging condition.

A stereoscopic X-ray apparatus according to the present invention comprises means for irradiating X-rays in two directions to an object to be examined; means for picking-up images created by X-rays having passed the object to provide X-ray images picked-up in the two directions; means for detecting the positional relation of the object with respect to the irradiation means and picking-up means; and means for adjusting the positional relation between two X-ray images output from the picking-up means according to the positional relation of the object detected by the detection means and then stereoscopically displaying the X-ray images.

According to the present invention, a distance between display positions of the two X-ray images output from the picking-up means is adjusted to a distance corresponding to desired stereoscopy and then the X-ray images are displayed in a stereoscopic manner so that desired stereoscopy can always be attained irrespective of the imaging condition.

Additional objects and advantages of the present invention will be set forth in the description which follows, and in part will be obvious from the description, or may be learned by practice of the invention. The objects and advantages of the present invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the present invention and, together with the general description given above and the detailed description of the preferred embodiments given below, serve to explain the principles of the invention in which:

FIG. 3 is a block diagram of a first embodiment of a stereoscopic X-ray apparatus according to the present invention;

FIGS. 4A, 4B and 4C are diagrams for explaining the operation of the first embodiment;

FIG. 5 is a block diagram of a second embodiment of a stereoscopic X-ray apparatus according to the present invention;

DETAILED DESCRIPTION OF THE PREFERRED EMBODIMENTS

Figure 1C:
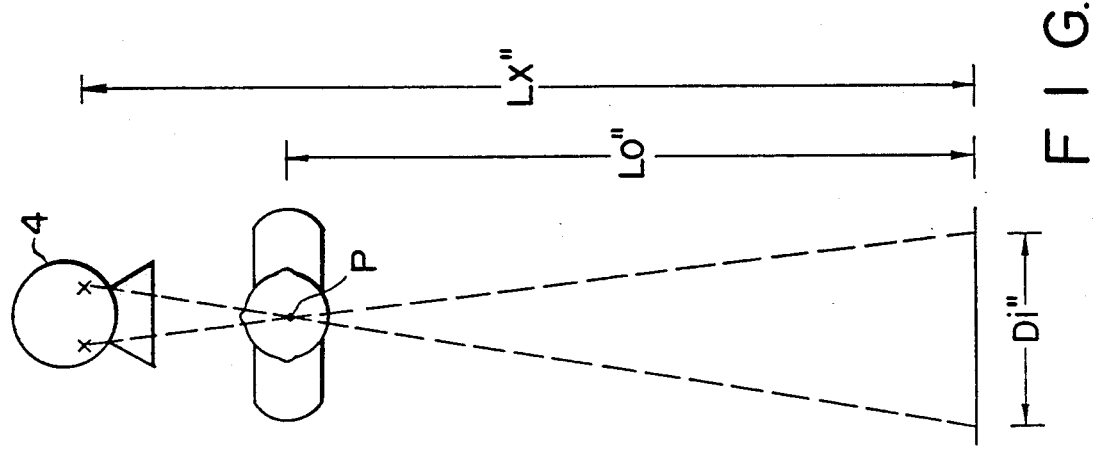
FIGS. 1A, 1B and 1C are diagrams for illustrating the stereoscopy at the time of stereoscopic pick-up of an X-ray image according to the present invention.

There will now be described preferred embodiments of a stereoscopic X-ray apparatus according to the present invention with reference to the accompanying drawings. First, the principle of the present invention is explained It is assumed that desired stereoscopy is obtained with the positional relation among an object 2 to be examined, stereoscopic X-ray tube 4, and image pick-up plane 6 (input fluorescent screen of an image intensifier tube) set as shown in FIG. 1A. At this time, a distance Di between two images of a point P in the object 2 created by X-rays irradiated from the right and left foci of the X-ray tube 4 corresponding to parallax between the two images relating to the stereoscopy can be derived as follows.

That is, the following equation can be obtained if the convergence angle between the two X-rays is $\theta$.

$$\tan \theta = Df/(Lx - Lo) = Di/Lo \quad (1)$$

where Df indicates a distance between the right and left foci of the X-ray tube 4, Lx indicates a distance between the right and left foci of the X-ray tube 4 and the image pick-up plane 6, and Lo indicates a distance between the object point P and the image pick-up plane 6.

The distance Di between the two images picked-up on the plane 6 can be expressed as follows by rewriting the equation (1).

$$D = Df \times Lo/(Lx - Lo) \quad (2)$$

Figure 1A:
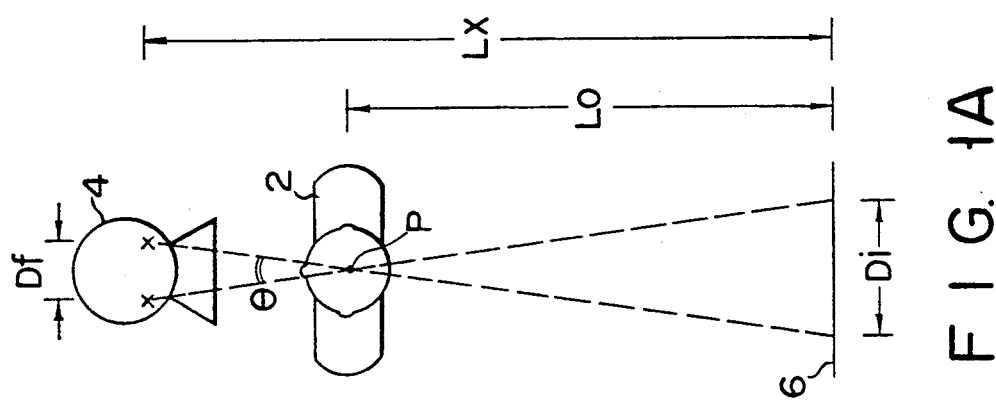
Figure 2A:
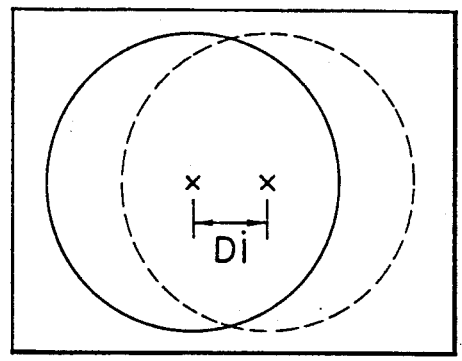
FIGS. 2A, 2B and 2C are diagrams respectively showing stereosoopio display states in the cases of FIGS. 1A, 1B and 1C.

At this time, the stereoscopic display state shown in FIG. 2A is obtained if two images are alternately displayed on one display unit. In this case, the right and left images displayed are deviated from each other in a horizontal direction on the same display unit, thus causing parallax between the right and left images and permitting the X-ray image of the object to be stereoscopically observed An observer can observe the same positional relation of the blood vessel and organizations from a view point of anatomy in the stereoscopic display under the desired stereoscopy as he or she observe the living body. Therefore the positional relation as shown in FIG. 1A is called a standard positional relation.

Figure 2B:
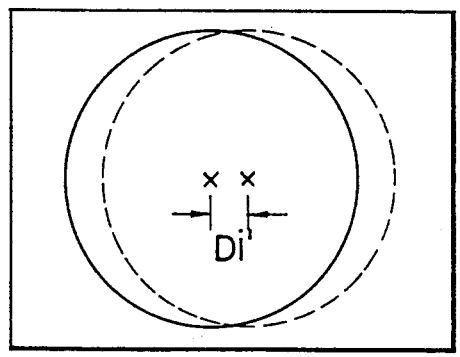

If only the object 2 is moved towards the image pick-up plane 6 with the distance Lx between the right and left foci of the X-ray tube 4 and the image pick-up plane 6 kept unchanged in the standard positional relation as shown in FIG. 2B, the distance between the object point P and the image pick-up plane is changed to Lo' so that the distance (=Di') between the right and left images on the pick-up plane 6 becomes smaller than Di. As a result, the distance Di' between the right and left images corresponding to the parallax becomes smaller than that set in the standard positional relation as shown in FIG. 2B, and therefore the stereoscopy becomes weak. In order to compensate for reduction in the stereoscopy, the distance between the two images may be set to be larger when the two images are displayed. That is, the left image is shifted to the right and the right image is shifted to the left and then the images are displayed. As a result, the distance Di' between the images can be substantially increased, thereby making it possible to provide the same stereoscopy as in the case of FIG. 1A.

Figure 2C:
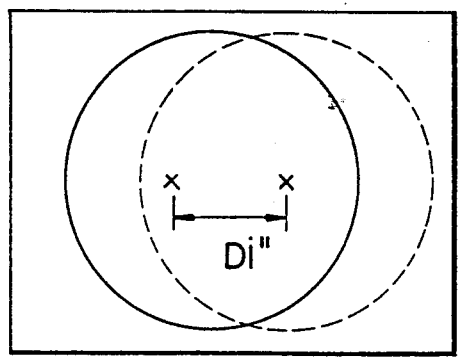

In contrast, when the distance Lx" between the X-ray tube 4 and the image pick-up plane 6 becomes longer than Lx with the distance between the object point P and the right and left foci of the X-ray tube 4 kept unchanged as shown in FIG. 1C, the distance (=Di") between the right and left images on the pick-up plane 6 becomes longer than Di as shown in FIG. 2C. Also, in this case, if the distance Di" becomes excessively long, the stereoscopy becomes too strong to attain the desired stereoscopy. In order to compensate for this, the two images may be shifted to come closer to each other when they are displayed. Thus, the distance Di" between the images can be substantially reduced, making it possible to attain the same stereoscopy as in the case of FIG. 1A.

FIGS. 2A to 2C show a case where the images are dynamically and stereoscopically displayed on one display unit, but when two display units are used to effect the static stereoscopic display, it is also possible to shift two images in the same manner as described above and then display the two images on two display units.

Now, the construction of the first embodiment of the present invention based on the above-described principle is explained with reference to FIG. 3. A stereoscopic X-ray tube 12 having two foci separated by a preset distance from each other is disposed above an object 10 to be examined and lying on a bed (not shown). An image intensifier tube 14 and a TV camera 16 are integrally arranged below the object 10. The X-ray tube 12 alternately irradiates X-rays from the two foci towards the object 10.

An X-ray image of the object 10 incident on the image intensifier tube 14 is converted to an optical image and picked-up by the TV camera 16. An image signal from the TV camera 16 is supplied to an image memory 20 via an A/D converter 18. The image memory 20 includes two frame memories 20a and 20b for storing respective X-ray images of the object 10 based on X-rays irradiated from the right and left foci of the X-ray tube 12. An output of the image memory 20 is supplied to a display unit 24 via a D/A converter 22. That is, output images of the frame memories 20a and 20b are alternately displayed on the display unit 24. Images on the display unit 24 are observed though field switcher glasses 26 with electronic shutters driven in synchronism with the alternate display operation.

The positional relation among the X-ray tube 12, image intensifier tube 14, and object 10, that is, a distance between the image intensifier tube 14 and the object 10 and a distance between the image intensifier tube 14 and the X-ray tube 12 are changed according to the image pick-up condition and thus are detected by a position detector 28. The detection results are supplied to a read/write controller 30 for the image memory 20. A system controller 34 for synchronizing the entire control operations is connected to the glasses 26, read/write controller 30 and a high tension generator 32 to irradiate the X-ray.

The operation of the first embodiment is explained with reference to FIGS. 4A to 4C. First, a distance between the object 10 and the image intensifier tube 14 and a distance between the X-ray tube 12 and the image intensifier tube 14 are detected by the position detector 28 and the detection results are supplied to the read/write controller 30. The memory 20 is set into the write-in mode, X-rays are alternately irradiated from the two foci and X-ray images thus created are written into the respective frame memories 20a and 20b. In this example, suppose that a left image created by the X-ray irradiated from the focus located on the right side when supplied from the TV camera 16 is stored into the frame memory 20a and a right image created by the X-ray irradiated from the focus located on the left side is stored into the frame memory 20b.

Next, the memory 20 is set into the readout mode (at this time, the object may be removed from the bed) and image data items are alternately read out from the frame memories 20a and 20b in synchronism with the frame period of the display unit 24, supplied to the display unit 24 via the D/A converter 22, and displayed on the display unit 24. Then, the system controller 34 controls the ON/OFF operation of the right and left electronic shutters of the glasses 26 in synchronism with the operation of reading out data from the frame memories 20a and 20b so as to permit the left and right images to impinge on the left and right eyes, respectively. As a result, parallax occurs between the two images observed by the right and left eyes and the observer can stereoscopically observe the X-ray images of the object.

However, under this condition, the parallax is determined by the positional relation of the object set at the image pick-up time and it is sometimes impossible to attain desired stereoscopy. Therefore, the read/write controller 30 checks the stereoscopy (distance between the right and left images) at the image pick-up time based on the positional relation among the X-ray tube 12, object 10, and image intensifier tube 14 detected by the position detector 28 and checks whether it is equal to the distance Di in the standard positional relation or not. If it is detected that it is not equal to the distance Di, the two images are shifted in a horizontal direction to adjust the distance between the two images. Shift of the image in a horizontal direction may be effected by changing readout addresses with respect to the write-in addresses for the image memory 20. Since the distance between the images is determined by the relative positions of the images, it is possible to shift only one of the images to adjust the distance. However, in order to prevent the image being out of the screen by the image shift, in this example, the right and left images are shifted in opposite directions by the same distance equal to half the difference between the distance set at the image pick-up time and the distance set in the standard positional relation.

Figure 1B:
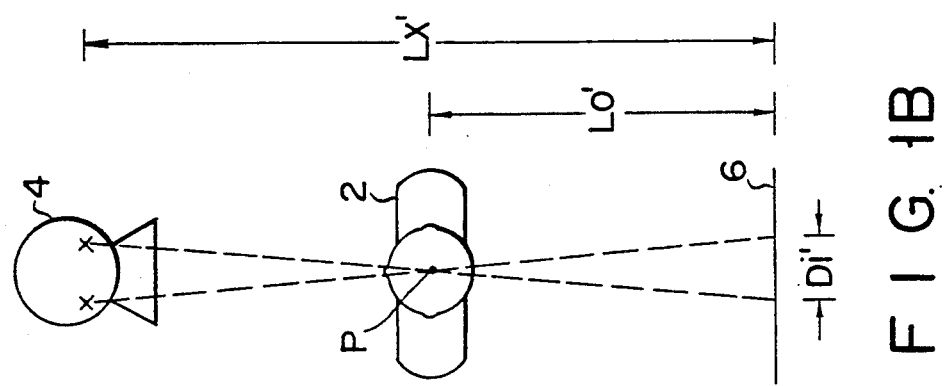

It is assumed now that the positional relation of the object at the image pick-up time is shown in FIG. 1C and an example of display as shown in FIG. 4B is obtained at this time. Further, it is assumed that an example of display obtained in the standard positional relation is shown in FIG. 4A. At this time, the shift amount $\Delta$ is $(Di'' - Di)/2$. Therefore, as shown in FIG. 4C, if the left and right images are read out after being shifted by $\Delta$ in the right and left directions, respectively, the same stereoscopy as is obtained in the standard positional relation can be attained irrespective of the positional relation among the object, X-ray tube, and image intensifier tube set at the image pick-up time. At this time, if $Di''$ is smaller than Di as shown in FIG. 1B, $\Delta$ becomes negative so that the left image may be read out after being shifted by $-\Delta$ in the right direction, that is, after being shifted by $\Delta$ in the left direction and the right image may be read out after being shifted by $-\Delta$ in the left direction, that is, after being shifted by $\Delta$ in the right direction. Also, in this case, the same stereoscopy as is obtained in the standard positional relation shown in FIG. 1A can be attained.

As described above, according to the first embodiment, X-ray images of the object are picked-up based on X-rays irradiated from the right and left foci of the X-ray tube 14 and stored into the frame memories, and the stored X-ray images are alternately read out from the frame memories and alternately displayed on the same display unit. The displayed images are observed through the glasses with electronic shutters driven in synchronism with the alternate display operation so that the stereoscopic image of the object can be observed. At the time of display, the positional relation of the object at the image pick-up time is checked and if it is detected that the standard positional relation is not attained, the two images are displayed after being horizontally shifted in order to compensate for deviation in the stereoscopy, so that stereoscopic display can always be obtained with desired stereoscopy.

In the first embodiment, the dynamic stereoscopic display using one display unit is explained, but it is also possible to effect the static stereoscopic display for simultaneously displaying the two images on two display units positioned right and left. Further, in the first embodiment, the stereoscopic X-ray tube is used to obtain right and left X-ray images, but it is also possible to use a normal single-focus type X-ray tube, and in this case, the X-ray tube is revolved by a preset angle with the object set as its revolution center and X-rays are irradiated before and after the revolution. Further, the image intensifier tube is used to pick-up X-ray images which have passed the object, but it is also possible to photograph the X-ray images, read out the image information by means of an image reader, for example, and then store the image information into an image memory. In this case, the preset angle of revolution corresponds to the parallax of the images. Therefore, it is necessary to input the angle to the read-write controller 30.

Now, the other embodiments are explained. In these embodiments, the same portions as those shown in the first embodiment are denoted by the same reference numerals and the detail explanation therefore is omitted. FIG. 5 is a block diagram showing the second embodiment. The second embodiment is similar to the first embodiment except that an image enlargement circuit 40 is connected between the image memory 20 and D/A converter 22.

Figure 6A:
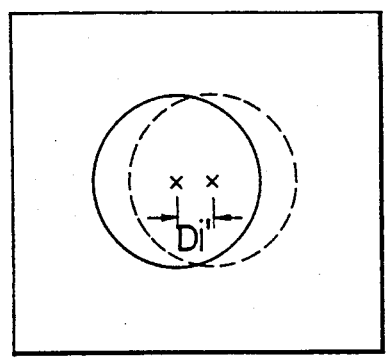
FIGS. 6A and 6B are diagrams for explaining the operation of the second embodiment in order to explain the effect of the second embodiment.
Figure 6B:
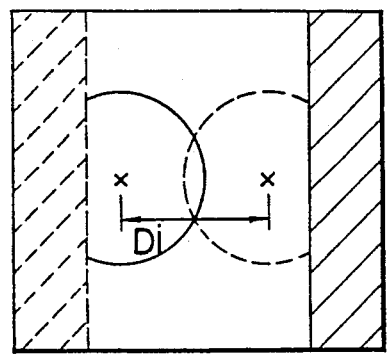

In the first embodiment, if the positional relation shown in FIG. 1B is set, a distance Di' between the two images becomes smaller than a distance Di set in the standard positional relation as shown in FIG. 6A, and in order to attain the same stereoscopy as in the standard positional relation, it is necessary to shift the two images so as to increase the distance between the two images. In this case, the left end of the right image frame enters the left image to cut away the left portion of the left image as shown by a hatched portion of broken lines in FIG. 6B. Likewise, the right end of the left image frame enters the right image to cut away the right portion of the right image as shown by a hatched portion of solid lines in FIG. 6B.

Figure 7A:
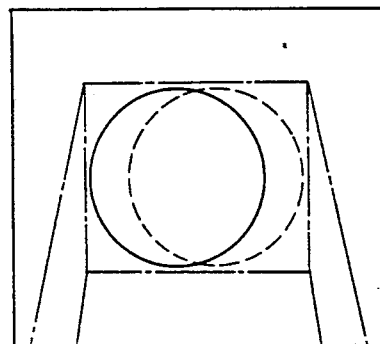
FIGS. 7A, 7B and 7C are diagrams for explaining the operation of the second embodiment.
Figure 7B:
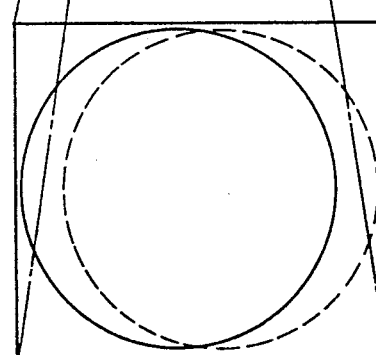
Figure 7C:
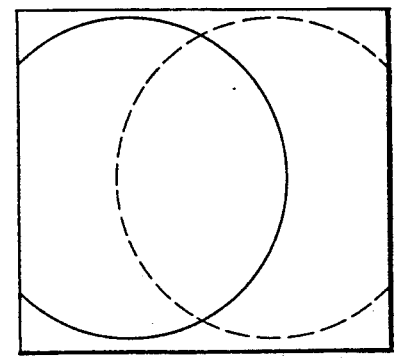

In order to solve this problem, in the second embodiment, an output image from the image memory 20 shown in FIG. 7A is enlarged as shown in FIG. 7B by means of the image enlargement circuit 40. As a result, even if the two images are shifted to increase the distance therebetween, although the side portions of the images may extend outwardly of the screen of the display as shown in FIG. 7C and may not be displayed, the right and left end portions of the display screen does not cover the images so that part of the image will not be deleted and the effective display area of the image will not be reduced. The magnifying factor of the enlargement circuit 40 is so set that part of the image which is required to be positively observed may be displayed in the entire area of the display screen.

Figure 8:
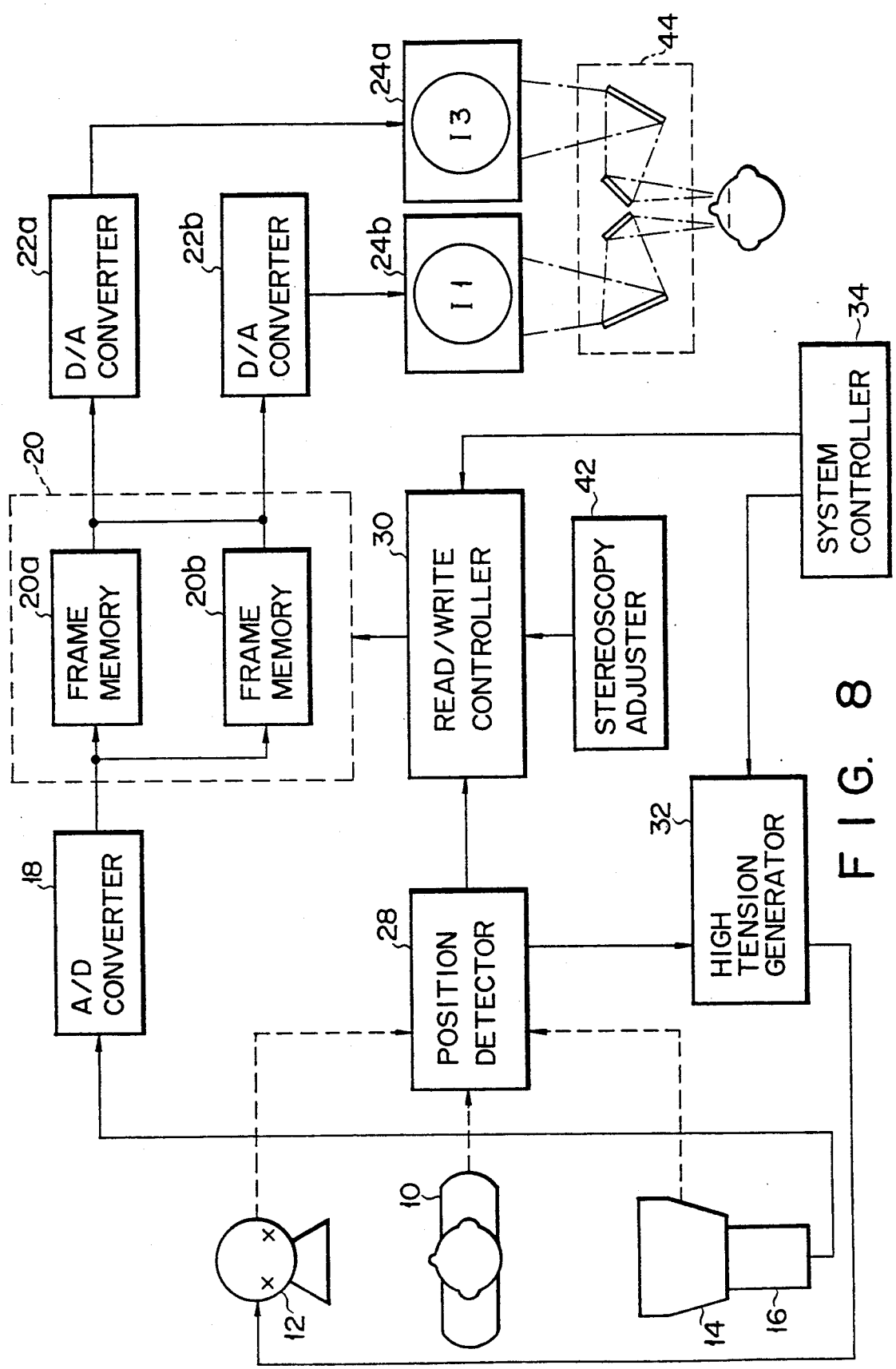
FIG. 8 is a block diagram of a third embodiment of a stereoscopic X-ray apparatus according to the present invention.

FIG. 8 is a block diagram showing the third embodiment. The third embodiment differs from the first embodiment in that an adjuster 42 capable of adjusting the sensitivity of stereoscopy is connected to the read/write controller 30 and the static stereoscopic display method of simultaneously displaying two images on two display units is used. In the above-described embodiments, the distance between the two images picked-up and displayed on the display screen is automatically adjusted to be set equal to the distance set in the standard positional relation as shown in FIG. 1A, but since the standard state in which the best stereoscopy is obtained may be different from person to person, the adjuster 42 is used to adjust the parallax (distance Di between the images) in this embodiment. Further, outputs of the frame memories 20a and 20b are respectively supplied to the display units 24a and 24b via the D/A converters 22a and 22b at the same time. Then, the images are observed by the right and left eyes through a stereoscopic viewer 44 for guiding the display images on the right and left display units 24a and 24b to the right and left eyes, thereby permitting the object to be stereoscopically observed.

As described above, according to the stereoscopic X-ray apparatus of the present invention, two images obtained by irradiating X-rays in two directions to the object can be set into the stereoscopic display state by setting them with a distance determined according to the positional relation between the object and the X-ray tube and image intensifier tube set at the image pick-up time, and as a result, the stereoscopy at the time of stereoscopic display can be adjusted irrespective of the position of the object after they are picked-up so that desired stereoscopy can be attained under any image pick-up condition. Further, a stereoscopic X-ray apparatus can be provided in which the stereoscopy can be changed by changing the distance between the two displayed images so that the positional relation in the depth direction between two things can be correctly recognized by any person.

The present invention is not limited to the above described embodiments, but can be variously modified. For example, instead of directly picking-up an output image of the image intensifier tube by use of the TV camera, the output image may be photographed on a film and image data on the film is read out by an image reader or the like after it is developed and then stored into an image memory A single-focus X-ray tube may be used as the X-ray tube instead of the stereoscopic X-ray tube, and in this case, X-rays are sequentially irradiated in two different directions set at different times Further, in the drawing, X-rays are irradiated from a position set above the object but can be irradiated from a position set under the object. In this case, the images obtained from the X-rays emitted from the right and left foci must be impinged on the left and right eyes, respectively so as to observe the front view of the object which is the standard for the diagnosis.

What is claimed is:

1. A stereoscopic X-ray apparatus comprising:
   means for irradiating X-rays in two directions to an object to be examined;
   means for picking-up images created by X-rays having passed said object to provide X-ray images picked-up in the two directions;
   means for detecting the positional relation of the object with respect to said irradiation means and picking-up means; and
   stereoscopic display means for adjusting the positional relation between two X-ray images output from said picking-up means according to the positional relation of said object detected by said detection means and stereoscopically displaying the X-ray images.

2. An apparatus according to claim 1, wherein said irradiating means is a stereoscopic X-ray tube having two foci and irradiating X-rays from the two foci in two directions intersecting at a target point in said object.

3. An apparatus according to claim 1, wherein said irradiating means includes an X-ray tube, means for revolving said X-ray tube around said object by a preset angle, and means for irradiating X-rays which intersect at a target point in said object from said X-ray tube before and after the revolution of said X-ray tube.

4. An apparatus according to claim 1, wherein said stereoscopic display means includes means for alternately displaying said two X-ray images on the same display screen.

5. An apparatus according to claim 4, further comprising glasses means to be put on an observer and having shutters driven to interrupt or transmit the image impinging on the right and left eyes of the observer in synchronism with the alternate display operation of said stereoscopic display means.

6. An apparatus according to claim 1, wherein said stereoscopic display means includes means for simultaneously displaying said two X-ray images side by side.

7. An apparatus according to claim 6, further comprising glasses means to be put on an observer, for guiding the right and left X-ray images to the right and left eyes of the observer 8. An apparatus according to claim 1, wherein said stereoscopic display means includes means for shifting at least one of the X-ray images picked-up in the two directions in the right or left direction to adjust a distance between said two X-ray images to be displayed.

9. An apparatus according to claim 8, wherein said stereoscopic display means includes means for enlarging the X-ray images and then shifting at least one of them.

10. An apparatus according to claim 1, wherein said stereoscopic display means includes a memory for storing X-ray images picked-up in two directions;
    and means for shifting the display position of the X-ray image in the right or left direction by changing the readout addresses for respective picture elements of the X-ray image in said memory with respect to the write-in addresses thereof.

11. An apparatus according to claim 1, wherein said stereoscopic display means includes means for detecting a distance between said object and said picking-up means and a distance between said irradiation means and said picking-up mean to detect a distance between said X-ray images on an image picking-up plane of said picking-up means;
    means for comparing said distance with a standard distance and deriving a difference therebetween; and
    means for shifting said two X-ray images in the right and left directions, respectively, by a distance equal to half the difference.

* * * * *